US011925418B2

(12) United States Patent
Peled et al.

(10) Patent No.: US 11,925,418 B2
(45) Date of Patent: Mar. 12, 2024

(54) METHODS FOR MULTI-MODAL BIOIMAGING DATA INTEGRATION AND VISUALIZATION

(71) Applicant: The General Hospital Corporation, Boston, MA (US)

(72) Inventors: Noam Peled, Charlestown, MA (US); Steven Stufflebeam, Charlestown, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 17/781,858

(22) PCT Filed: Dec. 2, 2020

(86) PCT No.: PCT/US2020/062900

§ 371 (c)(1), (2) Date: Jun. 2, 2022

(87) PCT Pub. No.: WO2021/113370

PCT Pub. Date: Jun. 10, 2021

(65) Prior Publication Data

US 2023/0008541 A1 Jan. 12, 2023

Related U.S. Application Data

(60) Provisional application No. 62/942,585, filed on Dec. 2, 2019.

(51) Int. Cl.
*G09B 19/24* (2006.01)
*A61B 34/10* (2016.01)
(Continued)

(52) U.S. Cl.
CPC .......... *A61B 34/10* (2016.02); *G01R 33/4806* (2013.01); *G03H 1/0005* (2013.01);
(Continued)

(58) Field of Classification Search
CPC .... G09B 23/28; G09B 23/285; G09B 23/283; G09B 23/32; G09B 19/00; G09B 19/003;
(Continued)

(56) References Cited

U.S. PATENT DOCUMENTS 9,788,905 B2 * 10/2017 Avisar .................... G09B 23/28
2012/0197619 A1 8/2012 Yelin et al.
(Continued)

FOREIGN PATENT DOCUMENTS

EP 2195676 B1 12/2016
WO 2021113370 A1 6/2021

OTHER PUBLICATIONS

International Search Report and Written Opinion for corresponding PCT Application No. PCT/US2020/062900, dated Feb. 2, 2020.
(Continued)

*Primary Examiner* — Robert J Utama
(74) *Attorney, Agent, or Firm* — Quarles & Brady LLP

(57) ABSTRACT

A multi-modal visualization system (MMVS) is provided, which may be used to analyze and visualize bioimaging data, objects, and pointers, such as neuroimaging data, surgical tools, and pointing rods. MMVS can integrate multiple bioimaging modalities to visualize a plurality of bioimaging datasets simultaneously, such as anatomical bioimaging data and functional bioimaging data.

22 Claims, 5 Drawing Sheets

110 Access Anatomical Imaging Data
120 Access Physiological/ Functional Imaging Data
130 Combine Anatomical and Physiological Image Data
140 Generate a Virtual Representation of a Subject Using the Combined Data
150 Access Object Image Data
160 Update Virtual Representation with Object Image Data
170 Display Updated Virtual Representation for a User

(51) Int. Cl.

| | |
|---|---|
| ***G01R 33/48*** | (2006.01) |
| ***G03H 1/00*** | (2006.01) |
| ***G06T 7/33*** | (2017.01) |
| ***G06T 19/00*** | (2011.01) |
| ***G09B 5/02*** | (2006.01) |
| ***G09B 23/30*** | (2006.01) |
| *A61B 90/00* | (2016.01) |

(52) U.S. Cl.

CPC ............ *G06T 7/344* (2017.01); *G06T 19/006* (2013.01); *G09B 5/02* (2013.01); *G09B 19/24* (2013.01); *A61B 2034/104* (2016.02); *A61B 2034/105* (2016.02); *A61B 2090/365* (2016.02); *G03H 2001/0061* (2013.01); *G06T 2207/30004* (2013.01); *G09B 23/30* (2013.01)

(58) Field of Classification Search

CPC . G09B 19/24; G09B 5/00; G09B 5/06; G09B 9/00; A61B 34/10; A61B 34/20; A61B 2034/105; A61B 2034/2065; A61B 2090/35; A61B 2090/367; A61B 2090/365

See application file for complete search history.

(56) References Cited

U.S. PATENT DOCUMENTS

| | | | | |
|---|---|---|---|---|
| 2014/0088941 | A1 | 3/2014 | Banerjee et al. | |
| 2017/0258526 | A1 | 9/2017 | Lang | |
| 2019/0080515 | A1* | 3/2019 | Geri | G06F 3/012 |
| 2019/0139236 | A1* | 5/2019 | Cheng | G16H 20/40 |
| 2019/0231436 | A1 | 8/2019 | Panse et al. | |
| 2019/0380792 | A1* | 12/2019 | Poltaretskyi | G16H 50/50 |

OTHER PUBLICATIONS

European Patent Office, Extended Search Report, Application No. 20895709.2, dated Oct. 25, 2023, 9 pages.

Felsenstein, O. et al., Multi-Modal Neuroimaging Analysis and Visualization Tool (MMVT), Dec. 20, 2019, 27 pages.

Peled, N. et al., MMVT—Multi-Modality Visualization Tool, GitHub Repository, 2017, https://github.com/pelednoam/mmvt, DOI:10.5281/zenodo.438343, 7 pages.

Peled, N. et al., pelednoam/mmvt: Stable Version, Published Mar. 7, 2018, 4 pages.

* cited by examiner

METHODS FOR MULTI-MODAL BIOIMAGING DATA INTEGRATION AND VISUALIZATION

CROSS-REFERENCE TO RELATED APPLICATIONS

This application represents the United States national stage entry of PCT International Application Serial No. PCT/US2020/062900, filed on Dec. 2, 2020, which claims the benefit of U.S. Provisional Patent Application Ser. No. 62/942,585, filed on Dec. 2, 2019, and entitled "Systems and Methods for Multi-Modal Bioimaging Data Integration and Visualization," which is incorporated herein by reference as if set forth in its entirety for all purposes.

STATEMENT REGARDING FEDERALLY SPONSORED RESEARCH

This invention was made with government support under W911NF-14-2-0045 awarded by Defense Advanced Research Projects Agency (DARPA). The government has certain rights in the invention.

BACKGROUND

Surgical planning currently suffers from different imaging modalities using different proprietary tools. These proprietary tools do not provide for any integration between different imaging modalities or manufactures and provide only limited computational analysis when compared to the challenges faced in the surgical setting. Conventional 3D tools do not readily answer clinical questions, such as when a surgeon asks, "What electrodes are close to the epileptic onset?"

Thus, there remains a need for improved and streamlined tools and processes to provide for less surgical errors and better surgical outcomes.

SUMMARY OF THE DISCLOSURE

The present disclosure addresses the aforementioned drawbacks by providing systems and methods for image data visualization. The systems and methods provided herein facilitate an understanding of anatomical and functional information in a manner provides for improved experience and clinical readiness.

In one configuration, a multi-modal visualization system (MMVS) is provided, which may be used to analyze and visualize anatomical and physiological or functional data along with, objects, such as healthcare or surgical tools. Integration of imaging data between modalities may be performed and may include use of an unified 3D interactive platform. Methods in accordance with the present disclosure may be automated or semi-automated to provide for a faster and more accurate pipeline, for example, create training systems for healthcare professionals.

In one configuration, a system is provided for simulating a medical procedure for a medical professional to carry out using a medical tool. The system includes a computer system configured to: (i) access anatomical imaging data acquired from a subject using a first imaging modality; (ii) access physiological imaging data acquired from a subject using a second imaging modality; and (iii) combine the first imaging data and the second imaging data to generate an integrated model of the subject. The system also includes a virtual reality and/or augmented reality system configured to: (i) generate a visual representation of the subject using the integrated model of the subject for a medical professional to experience; (ii) register, with the visual representation of the subject, a model of a medical tool corresponding to a medical tool used by the medical professional; (iii) update the visual representation of the subject based on a virtual interaction of the medical tool used by the medical professional with the visual representation of the subject using the model of the subject and the model of the medical tool; and (iv) generate an updated visual representation of the subject after the virtual interaction of the medical tool used by the medical professional with the visual representation of the subject using the model of the subject and the model of the medical tool to illustrate the medical procedure.

In another configuration, a method is provided for simulating a medical procedure for a medical professional to carry out using a medical tool. The method includes accessing, with a computer system, anatomical imaging data acquired from a subject using a first imaging modality. The method also includes accessing, with the computer system, physiological imaging data acquired from a subject using a second imaging modality. The method also includes combining, with the computer system, the first imaging data and the second imaging data to generate an integrated model of the subject. The method also includes generating, using a virtual reality or augmented reality system, a visual representation of the subject using the integrated model of the subject for a medical professional to experience using the virtual reality or augmented reality system. The method also includes registering, using the virtual reality or augmented reality system, with the visual representation of the subject, a model of a medical tool corresponding to a medical tool used by the medical professional using the virtual reality or augmented reality system. The method also includes updating, using the virtual reality or augmented reality system, the visual representation of the subject based on a virtual interaction of the medical tool used by the medical professional with the visual representation of the subject using the model of the subject and the model of the medical tool. The Method also includes generating, using the virtual reality or augmented reality system, an updated visual representation of the subject after the virtual interaction of the medical tool used by the medical professional with the visual representation of the subject using the model of the subject and the model of the medical tool to illustrate the medical procedure.

In yet another configuration, a method for visualizing image data of a subject is provided. The method includes accessing, with a computer system, anatomical imaging data acquired from a subject using a first imaging modality. The method also includes accessing, with the computer system, physiological imaging data acquired from a subject using a second imaging modality. The method also includes generating image fusion data by combining, with the computer system, the first imaging data and the second imaging data to generate an integrated model of the subject. The method also includes generating, using a virtual reality or augmented reality system, a visual representation of the subject using the integrated model of the subject for a medical professional to experience using the virtual reality or augmented reality system. The method also includes registering, using the virtual reality or augmented reality system, with the visual representation of the subject, a model of a medical tool corresponding to a medical tool used by the medical professional using the virtual reality or augmented reality system. The method also includes updating in real-time, using the virtual reality or augmented reality system, the visual representation of the subject based on a virtual interaction of the medical tool used by the medical professional with the visual representation of the subject using the model of the subject and the model of the medical tool. The Method also includes generating in real-time, using the virtual reality or augmented reality system, an updated visual representation of the subject after the virtual interaction of the medical tool used by the medical professional with the visual representation of the subject using the model of the subject and the model of the medical tool to illustrate the medical procedure.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

Figure 1:
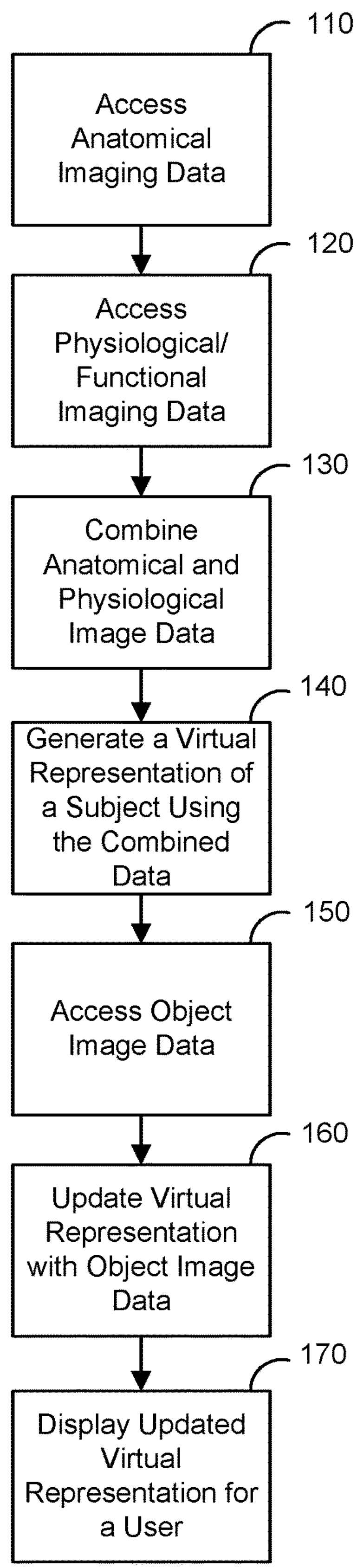
FIG. 1 is a flowchart of non-limiting example steps for a method for integrating and visualizing bioimaging data of a subject, according to the present disclosure.

Referring to FIG. 1, a flowchart of non-limiting example steps is provided for one embodiment of an image integration and visualization method. Anatomical imaging data may be accessed by a computer system at step 110. Physiological or functional imaging data may be accessed at step 120 by the computer system. Image fusion may be performed by combining the anatomical and physiological/functional imaging data at step 130. A virtual representation of the subject may be generated at step 140 based upon the combined image data. The virtual representation may be a 2D image, a 3D image, or may include a 3D hologram, and the like. Image data of an object, such as a surgical tool, may be accessed or acquired at step 150. The virtual representation of the subject may be updated with the object image data at step 160, and the updated virtual representation may be displayed for a user at step 170.

For the purposes of the present disclosure and accompanying claims, the term "real-time" or related terms are used to refer to and define a real-time performance of a system, which is understood as performance that is subject to operational deadlines from a given event to a system's response to that event. For example, real-time acquisition, processing, and/or displaying of data based on empirically-acquired signals may be triggered and/or executed simultaneously with or without interruption of a signal-acquisition procedure. Real-time may be defined as a clinical time scale where a process is completed on an order of time similar to performing a medical imaging When referring to a real (i.e., non-virtual) subject, object (including a tool or implantable), or pointer, the subject, object, or pointer is not preceded by the word "real." For example, a real scalpel is referred to as a "scalpel." When referring to a virtual (i.e., non-real) subject, object (including a tool or implantable), or pointer, the subject, object, or pointer is preceded by the word "virtual." For example, a virtual scalpel is referred to as a "virtual scalpel."

The term "anamotical imaging data" means data collected from medical imaging of anatomical structures of a subject. Anatomical imaging data includes, but is not limited to, unprocessed data, processed data (including pre-processed data and post-processed data), and a combination of unprocessed data and processed data.

The term "functional imaging data" or "physiological imaging data" means data collected from medical imaging of anatomical functions of a subject. Functional imaging data includes, but is not limited to, unprocessed data, processed data (including pre-processed data and post-processed data), and a combination of unprocessed data and processed data.

The term "bioimaging" means imaging of at least one biological material using at least one imaging modality.

The term "bioimaging data" means data collected from bioimaging. Bioimaging data includes, but is not limited to, unprocessed data, processed data (including pre-processed data and post-processed data), and a combination of unprocessed data and processed data. Bioimaging data can include anatomical data, functional/physiological data, and a combination thereof.

The term "bioimaging device" means a device that generates bioimaging data including, but not limited to, an MRI device, PET device, SPECT device, CT device, x-ray device, an ultrasound device, MEG device, EEG device, NIRS device, and the like.

The term "bioimaging modality" means a modality for recording biological data including, but not limited to, magnetic resonance imaging (MRI), positron emission tomography (PET), single-photon emission computed tomography (SPECT), computed tomography (CT), diffusion tensor imaging (DTI), magnetic resonance spectroscopy (MRS), x-ray, ultrasound, functional MRI (fMRI), magnetoencephalography (MEG), electroencephalogram (EEG), and near-infrared spectroscopy (NIRS).

The term "computer" means a device capable of receiving data, processing data, and/or outputting data. A computer can be stand-alone or embedded (i.e., part of a device, such as a visualization device).

The term "computer system" means one or more permanently or temporarily connected computers. The one or more computers can be connected wirelessly and/or by wire.

The term "implantable" means an item that can be fully or partially placed onto and/or into a subject including but not limited to an electrode, screw, bolt, rod, plate, stent, pacemaker, defibrillator, and filler (e.g., silicone and saline). An implantable can be removable or non-removable.

The term "integration computer" means a computer that is at least a part of an integration system.

The term "integration system" means a system comprising at least one computer for integrating at least two bioimaging modalities. An integration system can also integrate non-bioimaging data such as object data or pointer data.

The term "multi-modal visualization system" or "MMVS" means a system comprising at least one integration system and at least one visualization system. A non-limiting example of an MMVS is the multi-modal visualization tool.

The term "neuroimaging" means bioimaging wherein the biological material is at least one brain material.

The term "neuroimaging data" means data collected from neuroimaging. Neuroimaging data includes but is not limited to unprocessed data, processed data (including pre-processed data and post-processed data), and a combination of unprocessed data and processed data.

The term "object" means a tool, a medical tool, a surgical tool, or an implantable.

The term "object data" means data collected from an object including but not limited to location, direction, orientation, speed, and a combination thereof. For example, the object data may include space data and orientation data (i.e., 6-degrees of freedom data). Object data can be collected from, for example, at least one camera.

The term "pointer" means a device or other means for pointing and/or selecting including but not limited to a finger and a pointing device (e.g., laser pointer, pointing rod).

The term "pointer data" means data collected from a pointer including but not limited to location, direction, orientation, speed, and a combination thereof. For example, the object data may include space data and orientation data (i.e., 6-degrees of freedom data). Pointer data can be collected from, for example, at least one camera.

The term "processing" or "process" means any type of processing of any amount of data, including bioimaging data, which includes pre-processing and post-processing.

The term "subject" means at least a part of an animal including but not limited to a human or other mammal, fish, amphibian, reptile, and bird. Non-limiting examples of a subject include a human, human brain, dog, dog heart, fish, and fish gill.

The term "subject model" means a physically created (for example, a 3D-printed, injection molded) subject of a corresponding subject using one or more materials. The one or more materials can be selected to mimic the characteristics of the corresponding subject. A subject model can also be at least part of a corpse.

The term "surgical planning session" means at least a part of a recording of at least one user using and least one real or virtual object to interact with a virtual subject to simulate a surgical procedure on the corresponding subject.

The term "surgical training session" means using a surgical planning session for surgical training.

The term "synchronization computer" means a computer that, in non-limiting examples, synchronizes between (i) at least two visualization devices, (ii) at least one visualization device, at least one object, and at least one camera, (iii) at least one visualization device, at least one pointer, and at least one camera, and (iv) at least one visualization device, at least one object, at least one camera, and at least one pointer.

The term "transmission" or "transmit" means any type of transmission of any amount of data, including bioimaging data. Transmission may occur by any means including but not limited to wired transmission and/or wireless transmission.

The term "tool" means a tool including but not limited to a medical tool, a surgical tool, and the like, including but not limited to a scalpel, scissors, saw, mallet, forceps, clamp, retractor, and needle.

The term "virtual implantable" means a visual representation of an implantable.

The term "virtual object" means a visual representation of an object (i.e., a visual representation of a tool or visual representation of an implantable).

The term "virtual pointer" means a visual representation of a pointer including a virtual finger and a virtual pointing device. The term "virtual pointer" also includes but is not limited to a crosshair and cursor.

The term "virtual subject" means a visual representation of a subject.

The term "virtual surgery" or "simulated surgery" means interacting at least one virtual object with at least one virtual subject.

The term "virtual tool" means a visual representation of a tool.

The term "visual representation" means a two-dimensional (2D) and/or three-dimensional (3D) image, or hologram. A visual representation can be on any medium including but not limited to a screen, monitor, gas (including air), and liquid (including water). In a non-limiting example, a visual representation of a scalpel can be a hologram of the scalpel and/or an image of the scalpel displayed on a monitor.

The term "visualization device" means a device for creating a visual representation of bioimaging data including but not limited to an augmented reality (AR) device, a virtual reality (VR) device, a monitor, and a display including a holographic display. A visualization device can be a wearable or non-wearable device. A visualization device can include one or more embedded computers.

The term "visualization system" means one or more permanently or temporarily connected visualization devices. The one or more visualization devices can be connected wirelessly and/or by wire.

In one embodiment, an MMVS is provided to analyze and visualize bioimaging data, such as neuroimaging data. MMVS may integrate multiple bioimaging modalities to visualize at least two bioimaging datasets simultaneously. The bioimaging modalities include but are not limited to MRI, PET, SPECT, CT, DTI, MRS, x-ray, ultrasound, fMRI, MEG, EEG, and NIRS. The bioimaging datasets and bioimaging modalities may be integrated in MMVS to create a visual representation, for example, a 3D image. A user can interact with the visual representation to, for example, hide and show parts of the anatomy (anatomical bioimaging data) or select a subset of the functional data. In instances where functional data changes over time, the user can, for example, select a single time point or observe how the functional data changes over time.

An MMVS can be used in surgical meetings when surgical teams desire to understand integrations of bioimaging datasets. In applications related to diagnosing and treating (therapeutic applications), for example, epilepsy, surgeons need to decide whether to implant invasive electrodes, such as stereoelectroencephalography (sEEG), electrocorticography (ECoG), or deep brain stimulation (DBS), and whether to resect the region of the brain that is suspected to be the source of epileptic activity.

In some embodiments, MMVS includes a dedicated panel with one or more virtual objects (for example, surgical tools and/or implantables), where the user can select the one or more virtual objects and interact with a virtual subject (e.g., conduct virtual surgery). The virtual surgery will alter a virtual subject's anatomy in a manner reflective of actual surgery on a subject. In a non-limiting example of a neuroimaging application, surgical tools that are commonly used in brain surgeries in an operating room (OR) may be simulated.

In some embodiments, MMVS may include an augmented reality (AR) device and/or virtual reality (VR) device to display a virtual subject in 3D, using, for example, the HoloLens™ device (Microsoft Corporation, Redmond, Washington, USA). The AR and/or VR device can be synchronized with at least one other AR and/or VR device so that at least two users can view and interact with the same virtual object(s) and/or virtual subject(s). In some embodiments, users can also synchronize to a remote session and view and interact with the same virtual object(s) and/or virtual subject(s) as the remote user(s).

Figure 2:
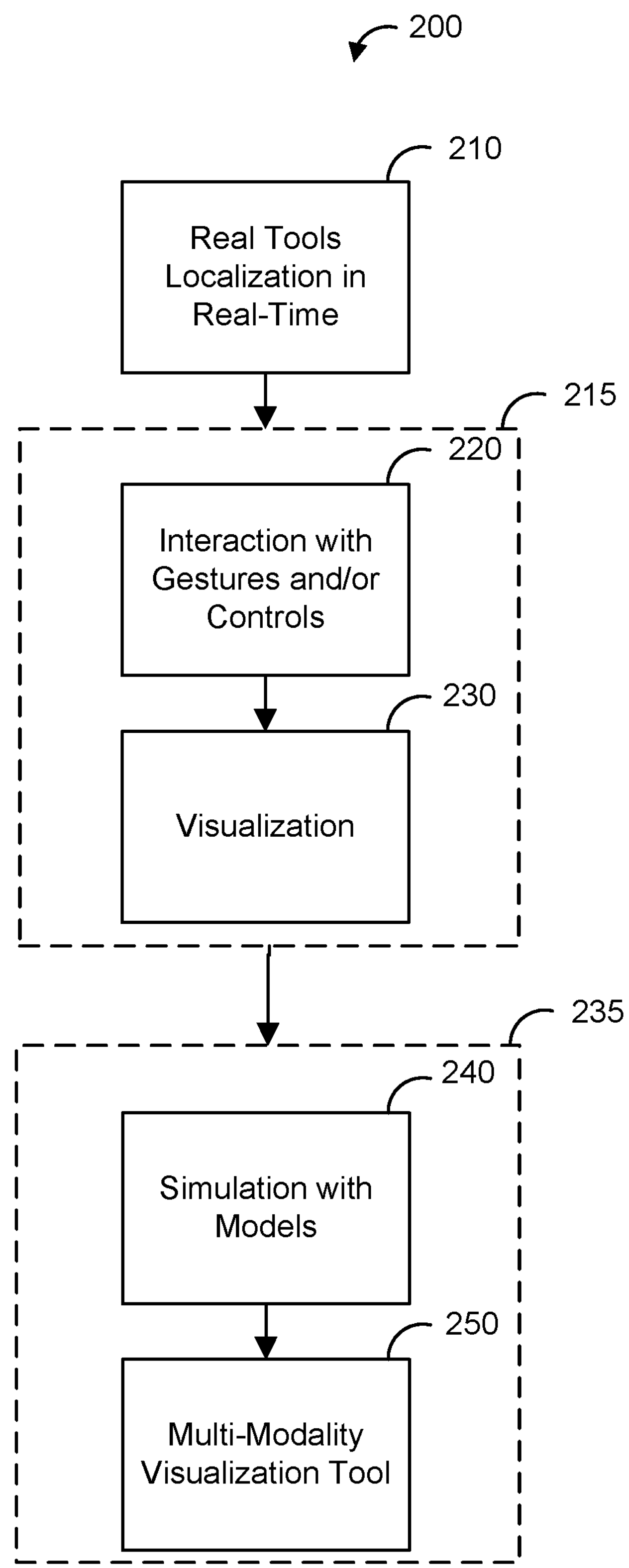
FIG. 2 is a flowchart of non-limiting example steps for a method for an augmented reality implementation in accordance with the present disclosure.

Referring to FIG. 2, a flowchart of a non-limiting example method 200 is shown. Real tools may be localized in real-time at step 210. Real-time interaction may then take place with an interface to step 215 where interaction with gestures, hand gestures, fingers, and/or controls may be performed at step 220. Visualization, such as with an AR app may be performed at step 230. Dynamic streaming to an interface at step 235 may be performed and include a surgery simulation with models at step 235 and may include a multi-modal visualization tool at step 250. In some configurations, the method 200 provides for an interactive AR app with real tools and with dynamic content.

In some embodiments, at least one camera may be used to detect at least one object in space (e.g., a scalpel). At least one visualization device may transmit object data to the MMVS when the object interacts with the virtual subject. The corresponding virtual subject may then be updated in MMVS and transmitted to the at least one visualization device.

In some embodiments, MMVS can be used in a surgical setting. In a non-limiting example, prior to a surgery, the subject (for example, a human subject's head) can be reconstructed from previously acquired bioimaging data (for example from an MRI scan) to create a virtual subject (for example, a virtual head). Using at least one camera, for example at least one high-resolution RGB camera, facial points on the subject's head can be detected, manually and/or automatically. These facial points on the subject can also be identified, manually and/or automatically, on the virtual subject, and the two sets of facial points can be used to co-register the subject to the virtual subject. Using the co-registration, the virtual subject can be overlaid on the subject (i.e., the virtual head overlaid on the head) such that they coexist in the same location in space. In a neurosurgery application, functional bioimaging data (for example, functional bioimaging data acquired from an fMRI scan) can be used to detect functional regions (for example, language regions and networks) in the brain to aid in the surgical process (for example, to guide to or avoiding certain functional regions and/or blood vessels.) Alternative to overlaying the virtual subject (virtual head) on the subject (head), the virtual subject can be displayed near (such as adjacent to) the subject to allow for interaction with the virtual subject (for example, rotate, zoom in, zoom out, travel inside, hide one or more parts, and/or add layers of anatomical and/or functional bioimaging data) without obstructing the view of the subject. To benefit from both the overlaid and non-overlaid scenarios, the virtual subject can be moved between the overlay position and the non-overlaid position.

To transmit data, including bioimaging data, between an integration system and a visualization system wirelessly and/or by wire, a connection protocol can be used. The connection protocol can be any protocol that allows for the transmission of data, and it can be used to synchronize one or more visualization devices that are external to the integration system (for example, one or more AR and/or VR devices). In some neuroimaging applications, pre-processing is used to generate 3D surfaces (for example pial, dura, skin, and skull) from bioimaging data prior to transmission. In scenarios involving complicated 3D surfaces, like cortical surfaces, the resolution of the surface may be reduced for faster transmission as well as faster processing by the visualization device. The "Automatic Re-topology and UV Remapping" discloses an algorithm for reducing the resolution of complicated 3D surfaces.

A notification can be sent or transmitted between an integration system and a visualization system wirelessly and/or by wire. In a non-limiting example, an interaction between an object (for example, a scalpel) and a virtual subject can cause the generation and transmission of a notification from the visualization system (for example, at least one AR and/or VR device) to the integration system (for example, a stand-alone computer). The notification may cause the integration system to update the bioimaging data and transmit the updated bioimaging data back to the visualization system. Notifications can be transmitted, in non-limiting examples, from integration computer to integration computer, visualization device to visualization device, integration computer to visualization device, and/or visualization device to integration computer.

Real-time identification may be provided of real objects in space, location, and/or orientation. When a predefined surgical tool (a scalpel, in a non-limiting example) is identified and interacts with the hologram or subject representation, a notification may be sent to multi-modal visualization tool (MMVT), and MMVT may update the 3D patient's objects and stream the updated objects to the AR/VR application. A user, such as a neurosurgeon, may interact with the hologram using real objects (e.g. surgical tools) with real-time detection of the location/orientation of the real objects providing for real-time interaction between the real objects and the hologram.

Figure 3:
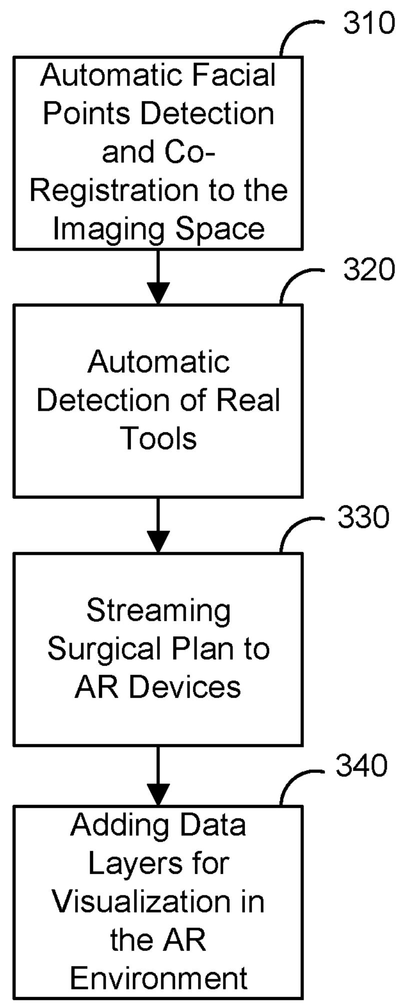
FIG. 3 is another flowchart of non-limiting example steps for a method for an augmented reality implementation in accordance with the present disclosure.

Referring to FIG. 3, a flowchart of a non-limiting example method for an augmented reality surgical training system is shown. Automatic facial points detection may be performed at step 310, and co-registration to the imaging space, such as an MR imaging space, may be performed. Automatic detection of real tools, such as surgical tools, may be performed at step 320. The surgical plan may be streamed to an AR device at step 330. Data layers, such as layers of information may be overlayed on a surgical environment for visualization at step 340.

In one embodiment, an MMVS system includes an integration computer, a monitor, a AR device worn by a user, and a virtual object. The integration computer may be wired to the monitor and wirelessly connected to the AR device. A virtual subject and the virtual object may be displayed on the monitor and the AR device. The user may use the virtual object to intersect with the virtual subject generating a notification to be sent from the AR device to the integration computer. Based on the nature of the intersection (such as direction, orientation, and speed, in non-limiting examples) and the type of object, the integration computer may update the bioimaging data to generate updated bioimaging data and transmits the updated bioimaging data to the AR device.

In one embodiment, an MMVS system includes an integration computer, a monitor, a synchronization computer, a first AR device worn by a first user, a second AR device worn by a second user, and a virtual object. The integration computer may be wired to the monitor and wirelessly connected to the two AR devices and the synchronization computer. The two AR devices may be wirelessly connected to the synchronization computer. A virtual subject and the virtual object are displayed on the monitor and the first AR device, and the second AR device. The first user may use the virtual object to intersect with the virtual subject generating a notification to be sent from the first AR device to the integration computer. Based on the nature of the intersection and the type of object, the integration computer may update the bioimaging data to generate updated bioimaging data and transmits the updated bioimaging data to the synchronization computer. The synchronization computer may then transmit the updated bioimaging data to the first AR device and second AR device.

In some embodiments, recording may be provided for a user(s) movements, object(s) used, virtual objects(s) used, pointer(s), notifications, and/or bioimaging data to create a surgical planning session. The surgical planning session may include how the bioimaging data is being updated over time. A surgical planning session may be downloaded from a database, which may be located on a local computer, a remote computer, and/or a cloud computer, and the like. Surgical planning sessions can be stored and retrieved for future repeat surgery(ies) on the same subject. A surgical team may view a surgical planning session to be better prepared and coordinated for an upcoming surgery. A surgical planning session may be used to better inform a patient about an upcoming surgery and allow for a more informed consent.

In some embodiments, a trainee may download a surgical planning session to be used for surgical training. The trainee can then practice his/her surgical skills to prepare for surgery. A trainer may access the surgical training session, synchronize the trainer's and the trainee's visualization devices, including remotely, and train the trainee.

In some embodiments, a teacher may download a surgical planning session to be used for surgical teaching. The teacher and each student may have a visualization device. The teacher can use a pointer, an object, and/or virtual object to interact with a virtual subject and transmit the virtual subject data, pointer data, object data, and/or virtual object data to each student's visualization device to instruct the students. The teacher may permit a student to interact with the virtual subject and transmit the virtual subject data, pointer data, object data, and/or virtual object data to the teacher's visualization device and the other students' visualization devices.

In some embodiments, the subject may be replaced with a subject model. In a non-limiting example, in a neurosurgery application, a surgeon can overlay a virtual human brain on a human brain model. One advantage may be that the surgeon can actually operate on the human brain model and provide lifelike feedback, such as haptic feedback, and the like.

In some embodiments, a user can wear haptic apparel (such as gloves, and the like) for lifelike feedback when interacting with a virtual subject.

Figure 4A:
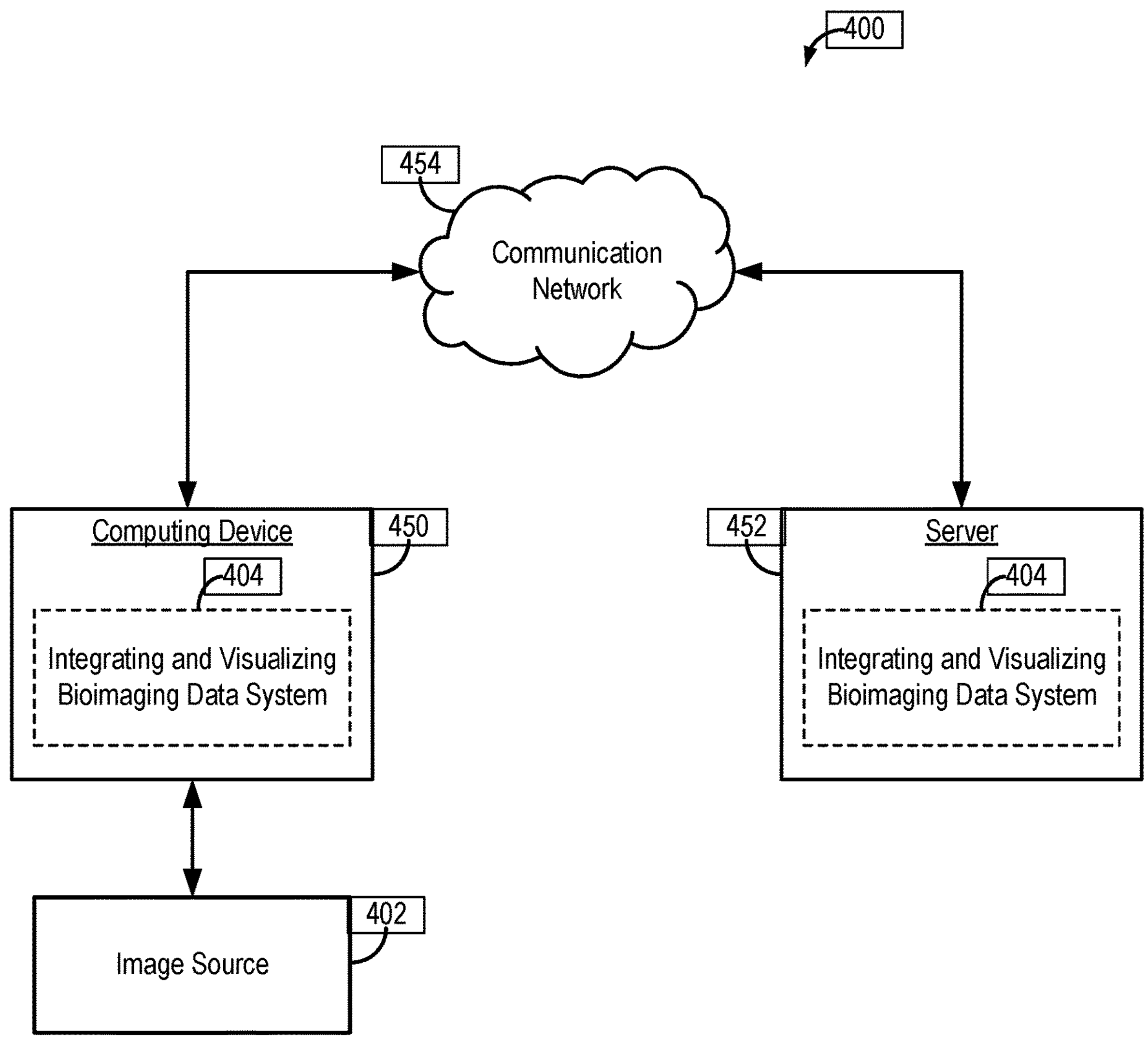
FIG. 4A is a block diagram of an example of a system for integrating and visualizing bioimaging data.

Referring now to FIG. 4A, an example of a system 400 for integrating and visualizing bioimaging data in accordance with some embodiments of the systems and methods described in the present disclosure is shown. As shown in FIG. 4A, a computing device 450 can receive one or more types of data (e.g., MRI, PET, SPECT, CT, DTI, MRS, x-ray, ultrasound, fMRI, MEG, EEG, NIRS data, and the like) from image source 402, which may be a source for the respective data, such as an imaging system. In some embodiments, computing device 450 can execute at least a portion of an integrating and visualizing bioimaging data system 404 to generate images, holograms, and/or models from data received from the image source 402.

Additionally or alternatively, in some embodiments, the computing device 450 can communicate information about data received from the image source 402 to a server 452 over a communication network 454, which can execute at least a portion of the integrating and visualizing bioimaging data system 404. In such embodiments, the server 452 can return information to the computing device 450 (and/or any other suitable computing device) indicative of an output of the integrating and visualizing bioimaging data system 404.

In some embodiments, computing device 450 and/or server 452 can be any suitable computing device or combination of devices, such as a desktop computer, a laptop computer, a smartphone, a tablet computer, a wearable computer, a server computer, a virtual machine being executed by a physical computing device, and so on. The computing device 450 and/or server 452 can also reconstruct images from the data.

In some embodiments, image source 402 can be any suitable source of image data (e.g., measurement data, images reconstructed from measurement data), such as an magnetic resonance imaging system, another computing device (e.g., a server storing image data), and so on. In some embodiments, image source 402 can be local to computing device 450. For example, image source 402 can be incorporated with computing device 450 (e.g., computing device 450 can be configured as part of a device for capturing, scanning, and/or storing images). As another example, image source 402 can be connected to computing device 450 by a cable, a direct wireless link, and so on. Additionally or alternatively, in some embodiments, image source 402 can be located locally and/or remotely from computing device 450, and can communicate data to computing device 450 (and/or server 452) via a communication network (e.g., communication network 454).

In some embodiments, communication network 454 can be any suitable communication network or combination of communication networks. For example, communication network 454 can include a Wi-Fi network (which can include one or more wireless routers, one or more switches, etc.), a peer-to-peer network (e.g., a Bluetooth network), a cellular network (e.g., a 3G network, a 4G network, etc., complying with any suitable standard, such as CDMA, GSM, LTE, LTE Advanced, WiMAX, etc.), a wired network, and so on. In some embodiments, communication network 454 can be a local area network, a wide area network, a public network (e.g., the Internet), a private or semi-private network (e.g., a corporate or university intranet), any other suitable type of network, or any suitable combination of networks. Communications links can each be any suitable communications link or combination of communications links, such as wired links, fiber optic links, Wi-Fi links, Bluetooth links, cellular links, and so on.

Figure 4B:
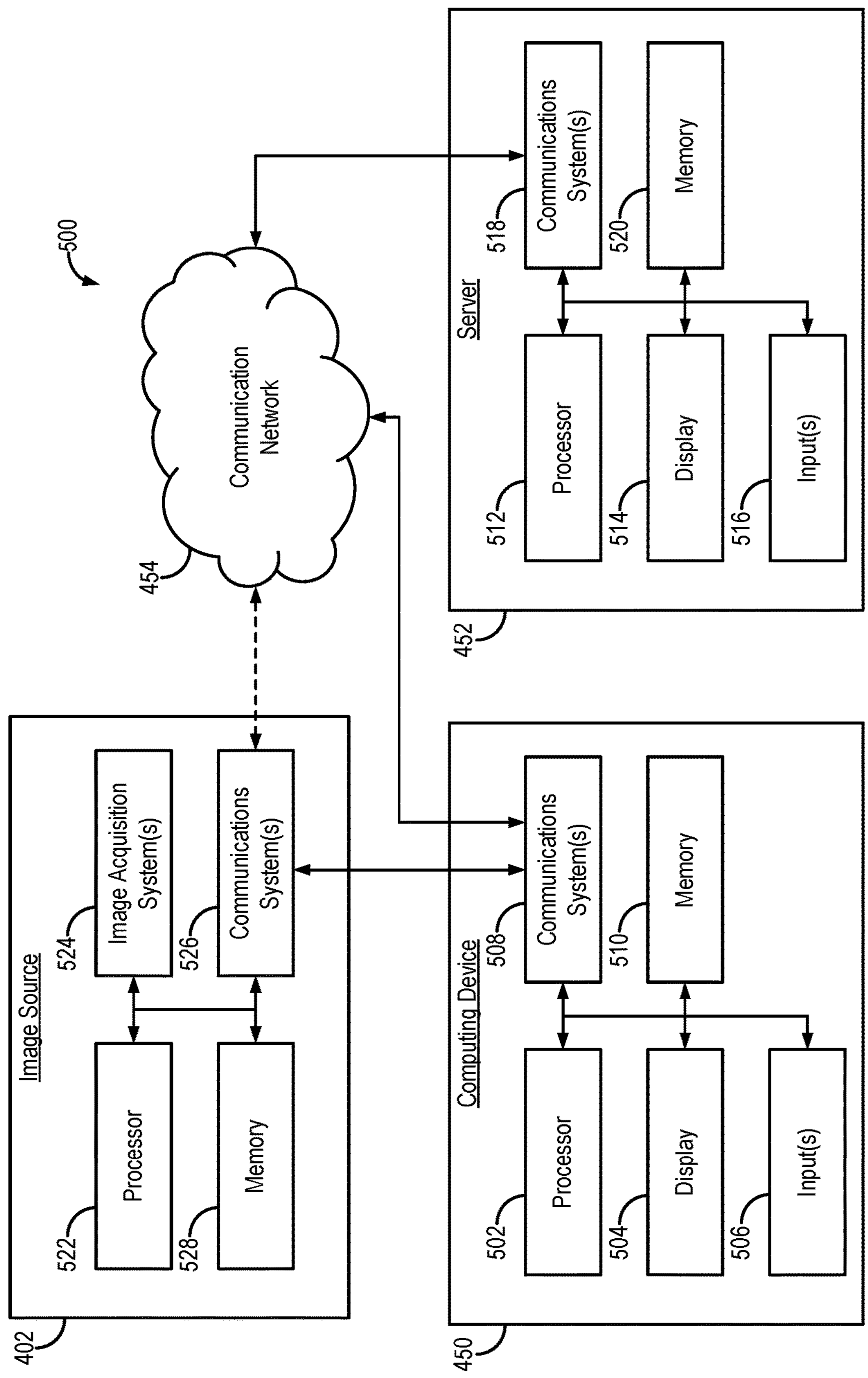
FIG. 4B is a block diagram of components that can implement the system for integrating and visualizing bioimaging data of FIG. 3A.

Referring now to FIG. 4B, an example of hardware 500 that can be used to implement image source 402, computing device 450, and server 452 in accordance with some embodiments of the systems and methods described in the present disclosure is shown. As shown in FIG. 4B, in some embodiments, computing device 450 can include a processor 502, a display 504, one or more inputs 506, one or more communication systems 508, and/or memory 510. In some embodiments, processor 502 can be any suitable hardware processor or combination of processors, such as a central processing unit ("CPU"), a graphics processing unit ("GPU"), and so on. In some embodiments, display 504 can include any suitable display devices, such as a computer monitor, a touchscreen, a television, and so on. In some embodiments, inputs 506 can include any suitable input devices and/or sensors that can be used to receive user input, such as a keyboard, a mouse, a touchscreen, a microphone, and so on.

In some embodiments, communications systems 508 can include any suitable hardware, firmware, and/or software for communicating information over communication network 454 and/or any other suitable communication networks. For example, communications systems 508 can include one or more transceivers, one or more communication chips and/or chip sets, and so on. In a more particular example, communications systems 508 can include hardware, firmware and/or software that can be used to establish a Wi-Fi connection, a Bluetooth connection, a cellular connection, an Ethernet connection, and so on.

In some embodiments, memory 510 can include any suitable storage device or devices that can be used to store instructions, values, data, or the like, that can be used, for example, by processor 502 to present content using display 504, to communicate with server 452 via communications system(s) 508, and so on. Memory 510 can include any suitable volatile memory, non-volatile memory, storage, or any suitable combination thereof. For example, memory 510 can include RAM, ROM, EEPROM, one or more flash drives, one or more hard disks, one or more solid state drives, one or more optical drives, and so on. In some embodiments, memory 510 can have encoded thereon, or otherwise stored therein, a computer program for controlling operation of computing device 450. In such embodiments, processor 502 can execute at least a portion of the computer program to present content (e.g., images, user interfaces, graphics, tables), receive content from server 452, transmit information to server 452, and so on.

In some embodiments, server 452 can include a processor 512, a display 514, one or more inputs 516, one or more communications systems 518, and/or memory 520. In some embodiments, processor 512 can be any suitable hardware processor or combination of processors, such as a CPU, a GPU, and so on. In some embodiments, display 514 can include any suitable display devices, such as a computer monitor, a touchscreen, a television, and so on. In some embodiments, inputs 516 can include any suitable input devices and/or sensors that can be used to receive user input, such as a keyboard, a mouse, a touchscreen, a microphone, and so on.

In some embodiments, communications systems 518 can include any suitable hardware, firmware, and/or software for communicating information over communication network 454 and/or any other suitable communication networks. For example, communications systems 518 can include one or more transceivers, one or more communication chips and/or chip sets, and so on. In a more particular example, communications systems 518 can include hardware, firmware and/or software that can be used to establish a Wi-Fi connection, a Bluetooth connection, a cellular connection, an Ethernet connection, and so on.

In some embodiments, memory 520 can include any suitable storage device or devices that can be used to store instructions, values, data, or the like, that can be used, for example, by processor 512 to present content using display 514, to communicate with one or more computing devices 450, and so on. Memory 520 can include any suitable volatile memory, non-volatile memory, storage, or any suitable combination thereof. For example, memory 520 can include RAM, ROM, EEPROM, one or more flash drives, one or more hard disks, one or more solid state drives, one or more optical drives, and so on. In some embodiments, memory 520 can have encoded thereon a server program for controlling operation of server 452. In such embodiments, processor 512 can execute at least a portion of the server program to transmit information and/or content (e.g., data, images, a user interface) to one or more computing devices 450, receive information and/or content from one or more computing devices 450, receive instructions from one or more devices (e.g., a personal computer, a laptop computer, a tablet computer, a smartphone), and so on.

In some embodiments, image source 402 can include a processor 522, one or more image acquisition systems 524, one or more communications systems 526, and/or memory 528. In some embodiments, processor 522 can be any suitable hardware processor or combination of processors, such as a CPU, a GPU, and so on. In some embodiments, the one or more image acquisition systems 524 are generally configured to acquire data, images, or both, and can include an ultrasound imaging system. Additionally or alternatively, in some embodiments, one or more image acquisition systems 524 can include any suitable hardware, firmware, and/or software for coupling to and/or controlling operations of an ultrasound imaging system. In some embodiments, one or more portions of the one or more image acquisition systems 524 can be removable and/or replaceable.

Note that, although not shown, image source 402 can include any suitable inputs and/or outputs. For example, image source 402 can include input devices and/or sensors that can be used to receive user input, such as a keyboard, a mouse, a touchscreen, a microphone, a trackpad, a trackball, and so on. As another example, image source 402 can include any suitable display devices, such as a computer monitor, a touchscreen, a television, etc., one or more speakers, and so on.

In some embodiments, communications systems 526 can include any suitable hardware, firmware, and/or software for communicating information to computing device 450 (and, in some embodiments, over communication network 454 and/or any other suitable communication networks). For example, communications systems 526 can include one or more transceivers, one or more communication chips and/or chip sets, and so on. In a more particular example, communications systems 526 can include hardware, firmware and/or software that can be used to establish a wired connection using any suitable port and/or communication standard (e.g., VGA, DVI video, USB, RS-232, etc.), Wi-Fi connection, a Bluetooth connection, a cellular connection, an Ethernet connection, and so on.

In some embodiments, memory 528 can include any suitable storage device or devices that can be used to store instructions, values, data, or the like, that can be used, for example, by processor 522 to control the one or more image acquisition systems 524, and/or receive data from the one or more image acquisition systems 524; to images from data; present content (e.g., images, a user interface) using a display; communicate with one or more computing devices 450; and so on. Memory 528 can include any suitable volatile memory, non-volatile memory, storage, or any suitable combination thereof. For example, memory 528 can include RAM, ROM, EEPROM, one or more flash drives, one or more hard disks, one or more solid state drives, one or more optical drives, and so on. In some embodiments, memory 528 can have encoded thereon, or otherwise stored therein, a program for controlling operation of image source 402. In such embodiments, processor 522 can execute at least a portion of the program to generate images, transmit information and/or content (e.g., data, images) to one or more computing devices 450, receive information and/or content from one or more computing devices 450, receive instructions from one or more devices (e.g., a personal computer, a laptop computer, a tablet computer, a smartphone, etc.), and so on.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (e.g., hard disks, floppy disks), optical media (e.g., compact discs, digital video discs, Blu-ray discs), semiconductor media (e.g., random access memory ("RAM"), flash memory, electrically programmable read only memory ("EPROM"), electrically erasable programmable read only memory ("EEPROM")), any suitable media that is not fleeting or devoid of any semblance of permanence during transmission, and/or any suitable tangible media. As another example, transitory computer readable media can include signals on networks, in wires, conductors, optical fibers, circuits, or any suitable media that is fleeting and devoid of any semblance of permanence during transmission, and/or any suitable intangible media.

The present disclosure has described one or more preferred embodiments, and it should be appreciated that many equivalents, alternatives, variations, and modifications, aside from those expressly stated, are possible and within the scope of the invention.

The invention claimed is:

1. A system for simulating a medical procedure for a medical professional to carry out using a medical tool, the system comprising:

a computer system configured to:

(i) access anatomical imaging data acquired from a subject using a first imaging modality;

(ii) access physiological imaging data acquired from a subject using a second imaging modality;

(iii) combine the first imaging data and the second imaging data to generate an integrated model of the subject;

one of a virtual reality and augmented reality system configured to:

(i) register the integrated model of the subject with the subject and generate a visual representation of the subject using the integrated model of the subject for a medical professional to experience using the one of virtual reality and augmented reality system;

(ii) register, with the visual representation of the subject, a model of a medical tool corresponding to a medical tool used by the medical professional using the one of virtual reality and augmented reality system;

(iii) update the visual representation of the subject based on a virtual interaction of the medical tool used by the medical professional with the visual representation of the subject using the model of the subject and the model of the medical tool;

(iv) generate an updated visual representation of the subject after the virtual interaction of the medical tool used by the medical professional with the visual representation of the subject using the model of the subject and the model of the medical tool to illustrate the medical procedure and (v) detecting facial points of the subject and registering the visual representation of the subject with the subject by co-registering the facial points of the subject and the anatomical imaging data.

2. The system of claim 1, wherein the visual representation includes at least one of a two-dimensional (2D) image or a three-dimensional (3D) image.

3. The system of claim 2, wherein the 3D image is a hologram.

4. The system of claim 1, wherein the virtual interaction of the medical tool includes a simulated surgical procedure.

5. The system of claim 1, wherein the medical tool includes at least one of a surgical tool or a medical implant.

6. The system of claim 1, wherein the medical tool includes at least one of a scalpel, a scissors, a saw, a mallet, a forceps, a clamp, a retractor, or a needle.

7. The system of claim 5, wherein the medical tool includes at least one of an electrode, a screw, a bolt, a rod, a plate, a stent, a pacemaker, a defibrillator, or a filler.

8. The system of claim 1, wherein the first imaging modality and the second imaging modality includes at least one of magnetic resonance imaging (MM), positron emission tomography (PET), single-photon emission computed tomography (SPECT), computed tomography (CT), diffusion tensor imaging (DTI), magnetic resonance spectroscopy (MRS), x-ray, ultrasound, functional MRI (fMRT), magnetoencephalography (MEG), electroencephalogram (EEG), and near-infrared spectroscopy (NIRS).

9. The system of claim 1, wherein the physiological imaging data includes functional MM (fMRT) data.

10. A method for simulating a medical procedure for a medical professional to carry out using a medical tool, the method comprising (i) accessing, with a computer system, anatomical imaging data acquired from a subject using a first imaging modality;

(ii) accessing, with the computer system, physiological imaging data acquired from a subject using a second imaging modality;

(iii) combining, with the computer system, the first imaging data and the second imaging data to generate an integrated model of the subject;

(iv) generating, using one of a virtual reality and augmented reality system, a visual representation of the subject using the integrated model of the subject for a medical professional to experience overlaid onto or adjacent to the subject using the one of virtual reality and augmented reality system;

(v) registering, using the one of virtual reality and augmented reality system, with the visual representation of the subject, a model of a medical tool corresponding to a medical tool used by the medical professional using the one of virtual reality and augmented reality system;

(vi) updating, using the one of virtual reality and augmented reality system, the visual representation of the subject based on a virtual interaction of the medical tool used by the medical professional with the visual representation of the subject using the model of the subject and the model of the medical tool;

(vii) generating, using the one of virtual reality and augmented reality system, an updated visual representation of the subject after the virtual interaction of the medical tool used by the medical professional with the visual representation of the subject using the model of the subject and the model of the medical tool to illustrate the medical procedure; and (viii) detecting facial points of the subject and registering the visual representation of the subject with the subject by co-registering the facial points of the subject and the anatomical imaging data.

11. The method of claim 10, wherein the visual representation includes at least one of a two-dimensional (2D) image or a three-dimensional (3D) image.

12. The method of claim 11, wherein the 3D image is a hologram.

13. The method of claim 10, wherein the virtual interaction of the medical tool is a simulated surgical procedure.

14. The method of claim 10, wherein the medical tool includes at least one of a surgical tool or an implantable device.

15. The method of claim 10, wherein the medical tool includes at least one of a scalpel, a scissors, a saw, a mallet, a forceps, a clamp, a retractor, or a needle.

16. The method of claim 10, wherein the medical tool includes at least one of an electrode, a screw, a bolt, a rod, a plate, a stent, a pacemaker, a defibrillator, or a filler.

17. The method of claim 10, wherein the first imaging modality and the second imaging modality includes at least one of magnetic resonance imaging (MM), positron emission tomography (PET), single-photon emission computed tomography (SPECT), computed tomography (CT), diffusion tensor imaging (DTI), magnetic resonance spectroscopy (MRS), x-ray, ultrasound, functional MRI (fMRT), magnetoencephalography (MEG), electroencephalogram (EEG), or near-infrared spectroscopy (NIRS).

18. The method of claim 10, wherein the physiological imaging data includes functional MM (fMRI) data.

19. A method for visualizing image data of a subject, comprising:

(i) accessing, with a computer system, anatomical imaging data acquired from a subject using a first imaging modality;

(ii) accessing, with the computer system, physiological imaging data acquired from a subject using a second imaging modality;

(iii) generating image fusion data by combining, with the computer system, the first imaging data and the second imaging data to generate an integrated model of the subject;

(iv) generating, using one of a virtual reality and augmented reality system, a visual representation of the subject using the integrated model of the subject for a medical professional to experience using the one of virtual reality and augmented reality system;

(v) registering, using the one of virtual reality and augmented reality system, with the visual representation of the subject, a model of a medical tool corresponding to a medical tool used by the medical professional using the one of virtual reality and augmented reality system;

(vi) updating in real-time, using the one of virtual reality and augmented reality system, the visual representation of the subject based on a virtual training interaction of the medical tool used by the medical professional with the visual representation of the subject using the model of the subject and the model of the medical tool;

(vii) generating in real-time, using the one of virtual reality and augmented reality system, an updated visual representation of the subject after the virtual interaction of the medical tool used by the medical professional with the visual representation of the subject using the model of the subject and the model of the medical tool to illustrate the medical procedure; and (viii) detecting facial points of the subject and registering the visual representation of the subject with the subject by co-registering the facial points of the subject and the anatomical imaging data.

20. The method of claim 19, wherein the virtual training interaction includes a simulated interventional procedure on the subject.

21. The system of claim 1, further comprising a camera configured to detect at least one of the subject or the medical tool.

22. The system of claim 1, further comprising an augmented reality device worn by a user and configured to display the visual representation of the subject and the model of the medical tool.

* * * * *

UNITED STATES PATENT AND TRADEMARK OFFICE
CERTIFICATE OF CORRECTION

PATENT NO. : 11,925,418 B2
APPLICATION NO. : 17/781858
DATED : March 12, 2024
INVENTOR(S) : Noam Peled et al.

It is certified that error appears in the above-identified patent and that said Letters Patent is hereby corrected as shown below:

In the Claims

Column 14, Claim 8, Line 16, “(MM)” should be --(MRI)--.

Column 14, Claim 8, Line 20, “(fMRT)” should be --(fMRI)--.

Column 14, Claim 9, Line 24, “MM (fMRT)” should be --MRI (fMRI)--.

Column 15, Claim 17, Line 20, “(fMRT)” should be --(fMRI)--.

Column 15, Claim 18, Line 24, “MM” should be --MRI--.

Signed and Sealed this
Eleventh Day of June, 2024

Katherine Kelly Vidal

Katherine Kelly Vidal
*Director of the United States Patent and Trademark Office*